(12) United States Patent
Bahar

(10) Patent No.: US 8,504,385 B2
(45) Date of Patent: Aug. 6, 2013

(54) PERSONALIZED NUTRITION ADVISOR

(76) Inventor: Mory Bahar, Georgetown, MA (US)

( * ) Notice: Subject to any disclaimer, the term of this patent is extended or adjusted under 35 U.S.C. 154(b) by 123 days.

(21) Appl. No.: 13/025,108

(22) Filed: Feb. 10, 2011

(65) Prior Publication Data

US 2011/0131240 A1 Jun. 2, 2011

Related U.S. Application Data

(63) Continuation of application No. 11/823,389, filed on Jun. 27, 2007, now abandoned.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | | | |
|---|---|---|---|---|
| 4,680,313 | A * | 7/1987 | Iwai | 514/627 |
| 7,076,438 | B1 * | 7/2006 | Tobelmann et al. | 705/7.32 |
| 2003/0059747 | A1 * | 3/2003 | Yoshida et al. | 434/127 |
| 2003/0182160 | A1 * | 9/2003 | Lahteenmaki | 705/2 |
| 2005/0048461 | A1 * | 3/2005 | Lahteenmaki | 435/3 |
| 2006/0074716 | A1 * | 4/2006 | Tilles et al. | 705/2 |
| 2007/0191689 | A1 * | 8/2007 | Elitok | 600/300 |
| 2008/0026106 | A1 * | 1/2008 | Weiss et al. | 426/72 |

* cited by examiner

*Primary Examiner* — Neha Patel
(74) *Attorney, Agent, or Firm* — Foley & Lardner LLP; Christopher J. McKenna

(57) ABSTRACT

The instant invention describes various computer program products and methods of using the same in order to provide personalized nutritional advice to end users.

4 Claims, No Drawings

PERSONALIZED NUTRITION ADVISOR

BACKGROUND OF THE INVENTION

Currently, when a patient is diagnosed with a particular medical condition, the physician provides him with a list of foods/nutrients to avoid and sometimes with a list of foods that would help treat the ailment. Given the interne culture, patients can often find more information and more lists of good vs. bad foods or nutrients online. However, patients' other possible medical conditions do not normally play a role in the physicians' "recommended foods or nutrients" list nor "foods or nutrients to avoid" list. As such, the patient might know what foods or nutrients to eat for the betterment of one of his medical conditions, but does not know if that same food or nutrient is beneficial or detrimental to a second or third medical condition from which he might be suffering.

This invention addresses a long felt need in the nutritional arena in that it provides a method for personalization of nutritional recommendations by taking into account the multitude of medical conditions from which a patient may be suffering.

BRIEF DESCRIPTION OF THE INVENTION

The invention is a novel method of providing nutritional guidance to people suffering from one or more medical conditions. The invention provides a method of ranking different nutrients according to their beneficial or harmful properties to a particular medical condition. The method can further take into account a multitude of different medical conditions and produce lists of good and bad nutrients by taking account of each medical condition separately and then combining the results to produce a master list of good vs. bad foods or nutrients for the person suffering from more than one medical condition.

DETAILED DESCRIPTION OF THE INVENTION

"Food": As used herein, food encompasses both natural foods and prepared dishes. Natural foods encompass dairy products, fish, poultry, meat, grains, nuts, seeds, legumes, herbs, spices, vegetables and fruits. Prepared dishes encompass processed foods such as sausage, lunch meat, as well as canned or frozen TV dinners, fast food such as hamburgers, fries, treats such as ice cream, pies, pastries, candies or foods prepared at home.

"Nutrient": As used herein, a nutrient is an element in a food item. It can be a vitamin, mineral, or any subpart present in a food item whether taken in its natural form in natural foods or as a nutritional supplement.

"Medical Condition": Any ailment, disorder or illness is considered a medical condition. Hypertension, Dyslipidemia, autoimmune diseases, inflammatory diseases, cardiovascular conditions, hereditary disorders and cancer, are only a few of the well-known examples. Desired life style changes such as following various weight loss programs and diets, training for sports and endurance events, and stress reduction are also examples of conditions "Database": For the purposes of this invention, database is used generically and is meant to encompass relational, hierarchical, network based, file based and object oriented database management systems.

"Item table": A table of all nutrients, food items, certain life style considerations such as exercise, smoking, recreational activities and alternative therapies.

"Problem table": A table of illnesses, health conditions, health risks, diets, and health goals.

"Content table": A table that maintains relationships between food items and various nutrients.

"Content Factor": A numerical value that represents the food item's level of richness of a particular nutrient. This Factor can have a value of 0 to 5 (or something similar) depending on richness of a particular nutrient in a food item. When possible, the Factor value can be set based on the established RDA for that particular nutrient.

"Remedy table": A table that maintains information about the relationship between entries in Item and Problem tables. There is a Factor that indicates whether an Item is good (a positive value) or bad (a negative value) for a Problem. The value of this factor (Remedy Factor) can be from −10 to +10 or something similar.

"Anti-Pro table": This table maintains the relationship between two different entries in the Item table. A Factor determines the nature of this relationship. If a food item or nutrient works against another, e.g., one nutrient interferes with the other nutrient's absorption, efficacy, body's increased demand for the other, or quicker excretion or metabolism of the other, the factor is negative. If a nutrient or a food item enhances the effects of another, e.g., facilitates absorption, increases efficacy of another, aids in the metabolism of another, then the factor is positive. This Factor (AP Factor) can have a value between −5 and +5 or equivalent.

"Group table": This table maintains information about grouping and hierarchical relationships that exist between entries in Item table, e.g., while both Fish and Tuna may be listed as entries in the Item table, it is important to note that Tuna is a member of Fish group.

"Original Entry" is an entry based on established scientific data, e.g., inherent qualities of a particular food item or scientific correlations between a particular food item or nutrient and a medical condition. In other words, an "Original Entry" is an entry not being generated by Procedures 1D, 2C, 3B and 4A. The "Original entries", the initial content of the database, are created from nutrition data available from the US government and the health industry as well as various studies on the relationship between diet and various health conditions.

"Procedure 1D": Creates new records within the Content table based on existing entries in the Content table for Groups as defined in the Group table. For example if the Beans and Legumes Group item is rich in Fiber (per an entry in Content table) then we create a record for every member of the Beans and Legumes Group (e.g., kidney beans) to reflect its richness in fiber.

"Procedure 2C": Creates new Remedy records based on entries in the Anti-Pro table. If Calcium is good for healthy bone and teeth (the Original Entry), then any food or nutrient that interferes with calcium absorption (as indicated in the Anti-Pro table) is listed as a new entry in the Remedy table with a negative factor value for the health of bones and teeth. The value of the factor depends on the value of the factor in the Original Entry and the value of the factor in the Anti-Pro table.

"Procedure 3B": Creates new Remedy records based on the presence of those remedy records that are between a Problem and a Group Item. For example if Fish is good for High Cholesterol (the Original Entry), and Tuna is a known member of the Fish Group then the system will automatically create a new Remedy record for Tuna (as member of the Fish group) and High Cholesterol. The factor for this new record is set based on the factor in the Original Entry.

"Procedure 4A": Creates new records within the Remedy table based on existing entries in the Remedy table and Content table. For example if Vitamin A is good for night vision (an existing entry within Remedy table or an Original Entry), then this procedure creates new records (or modifies existing records) that establish a positive (remedy) relationship between night vision (the Problem) and an Item that is rich in Vitamin A per an entry in Content table. The Remedy Factor is set (or adjusted upward or downward) based on the factor found in the Original Entry as well as the factor found in the corresponding Content table. Upon completion of the execution of this procedure, the remedy factor for each entry in the Remedy table reflects all known relationships between the nutrient content of that Item and the known relationship between those nutrients and the Problem.

"Derived Entries": The Procedures are executed in the order 1D through 4A as shown above. These procedures result in creation of additional entries in the database, which we will call Derived Entries. Upon execution of all these procedures we have a database that provides a complete mapping of all known relationships between various health conditions (i.e., all entries within the Problems table) and various food items (i.e., all entries in the Items table) and a goodness or badness score for each of these pairings (i.e., the Factor value in the Remedy table).

According to various embodiments, a method of providing personalized nutritional advice to a subject in need thereof is disclosed. The method can comprise: obtaining the subject's medical condition, querying a database for at least one of goodness and badness of particular foods and nutrients as they relate to said condition, quantifying said at least one of goodness and badness of particular foods and nutrients as it relates to said condition; producing at least one of a quantified goodness list and a quantified badness list of foods and nutrients, transmitting at least one of the said lists to the end user.

According to various embodiments, a method of providing personalized nutritional advice to a subject in need thereof is disclosed. The method can comprise obtaining the subject's medical condition, querying a database for goodness of particular foods and nutrients as they relate to said condition, querying a database for badness of particular foods and nutrients as they relate to said condition; quantifying said goodness as it relates to said condition; quantifying said badness as it relates to said condition; producing a quantified goodness list of recommended foods and nutrients; producing a quantified badness list of foods and nutrients to avoid, transmitting said two lists to the end user.

According to various embodiments, a method of providing personalized nutritional advice to a subject suffering from multiple medical conditions comprising is disclosed. The method comprises obtaining a list of the subject's medical conditions; querying a database for goodness of particular foods and nutrients as they relate to each condition; querying a database for badness of particular foods and nutrients as they relate to each condition; quantifying said goodness as it relates to each condition; quantifying said badness as it relates to each condition; producing a quantified goodness list of recommended foods and nutrients as it relates to each condition, producing a quantified badness list of foods and nutrients to avoid as it relates to each condition, re-ranking said quantified goodness lists and deriving a single list of recommended foods and nutrients; re-ranking said quantified badness lists and deriving a single list of foods and nutrients to avoid, transmitting said two single lists to the end user.

According to various embodiments, a method of providing a rating on a specific food item selected by the subject based on his unique health profile is disclosed. The method comprises: obtaining the subject's desired food item, querying a database for goodness of that particular food item as it relates to the subject's unique health profile, querying a database for badness of that particular food item as it relates to the subject's unique health profile; quantifying said goodness as it relates to the subject's unique health profile; quantifying said badness as it relates to the subject's unique health profile; producing a simple rating of Very Good, Good, Neutral, Unknown, Bad and Very Bad for the selected food item, transmitting said rating to the end user.

According to various embodiments, a method of providing suggestions within a desired group of foods as selected by the subject based on his unique health profile is disclosed. The method comprises: Obtaining the subject's desired group of food items, querying a database for goodness of all food items that are members of the said group as it relates to the subject's unique health profile, quantifying said goodness as it relates to the subject's unique health profile; sorting the list of said members based on their goodness rating, producing the optimal short list of food suggestions from within the desired group, transmitting said rating to the end user.

The list or lists described in each of the embodiments herein above can be transmitted through input-output devices, including but not limited to personal computer, cellular phone, smart phones, personal digital assistants, and a self-contained portable hand held computer device.

The invention also encompasses computer program products. According to various embodiments, the invention can be a computer program product for implementing, in a system including at least one processor and at least one data store configured to store one or more entries and configured to enable one or more end users, where each end user can invoke one of several methods to manipulate and eventually enable the end user to view one or more entries via the computer program product comprising a computer readable medium carrying computer executable instructions for implementing the method, a computer readable medium containing the data stores of one or more entries, and the computer executable instructions, when executed, causing the system to perform a method of providing personalized nutritional advice to a subject in need thereof comprising: obtaining the subject's medical condition, querying a database for at least one of goodness and badness of particular foods and nutrients as they relate to said condition, quantifying said at least one of goodness and badness of particular foods and nutrients as it relates to said condition; producing at least one of a quantified goodness list and a quantified badness list of foods and nutrients, transmitting at least one of the said lists to the end user.

According to various embodiments, the invention can be a computer program product for implementing, in a system including at least one processor and at least one data store configured to store one or more entries and configured to enable one or more end users, where each end user can invoke one of several methods to manipulate and eventually enable the end user to view one or more entries via the computer program product comprising a computer readable medium carrying computer executable instructions for implementing the method, a computer readable medium containing the data stores of one or more entries, and the computer executable instructions, when executed, causing the system to perform a method of providing personalized nutritional advice to a subject in need thereof comprising obtaining the subject's medical condition, querying a database for goodness of particular foods and nutrients as they relate to said condition, querying a database for badness of particular foods and nutrients as they relate to said condition; quantifying said goodness as it relates to said condition; quantifying said badness as it relates to said condition, producing a quantified goodness list of recommended foods and nutrients, producing a quantified badness list of foods and nutrients to avoid, transmitting said two lists to the end user.

According to various embodiments, the invention can be a computer program product for implementing, in a system including at least one processor and at least one data store configured to store one or more entries and configured to enable one or more end users, where each end user can invoke one of several methods to manipulate and eventually enable the end user to view one or more entries via the computer program product comprising: a computer readable medium carrying computer executable instructions for implementing the method, a computer readable medium containing the data stores of one or more entries, and the computer executable instructions, when executed, causing the system to perform a method of providing personalized nutritional advice to a subject suffering from multiple medical conditions comprising obtaining a list of the subject's medical conditions, querying a database for goodness of particular foods and nutrients as they relate to each condition, querying a database for badness of particular foods and nutrients as they relate to each condition; quantifying said goodness as it relates to each condition, quantifying said badness as it relates to each condition; producing a quantified goodness list of recommended foods and nutrients as it relates to each condition, producing a quantified badness list of foods and nutrients to avoid as it relates to each condition, re-ranking said quantified goodness lists and deriving a single list of recommended foods and nutrients; re-ranking said quantified badness lists and deriving a single list of foods and nutrients to avoid, transmitting said two single lists to the end user.

According to various embodiments, the invention can be a computer program product for implementing, in a system including at least one processor and at least one data store configured to store one or more entries and configured to enable one or more end users, where each end user can invoke one of several methods to manipulate and eventually enable the end user to view one or more entries via the computer program product comprising: a computer readable medium carrying computer executable instructions for implementing the method, a computer readable medium containing the data stores of one or more entries, and the computer executable instructions, when executed, causing the system to perform a method of altering behavior and improving lifestyle in a subject in need thereof comprising: obtaining the subject's desired nutrition and fitness goals, querying a database for goodness of particular life style choices as they relate to the health and fitness goals of the subject, querying a database for badness of particular life style choices as they relate to the health and fitness goals of the subject, quantifying said goodness as it relates to said health and fitness goals; quantifying said badness as it relates to said health and fitness goals; producing a quantified goodness list of optimal foods and activities; producing a quantified badness list of foods and activities to avoid; transmitting said two lists to the end user.

According to various embodiments, the invention can be a computer program product for implementing, in a system including at least one processor and at least one data store configured to store one or more entries and configured to enable one or more end users, where each end user can invoke one of several methods to manipulate and eventually enable the end user to view one or more entries via the computer program product comprising: a computer readable medium carrying computer executable instructions for implementing the method, a computer readable medium containing the data stores of one or more entries, and the computer executable instructions, when executed, causing the system to perform a method of providing a rating on a specific food item selected by the subject based on his unique health profile comprising: obtaining the subject's desired food item, querying a database for goodness of that particular food item as it relates to the subject's unique health profile, querying a database for badness of that particular food item as it relates to the subject's unique health profile; quantifying said goodness as it relates to the subject's unique health profile; quantifying said badness as it relates to the subject's unique health profile; producing a simple rating of Very Good, Good, Neutral, Unknown, Bad and Very Bad for the selected food item, transmitting said rating to the end user.

According to various embodiments, the invention can be a computer program product for implementing, in a system including at least one processor and at least one data store configured to store one or more entries and is configured to enable one or more end users, where each end user can invoke one of several methods to manipulate and eventually enable the end user to view one or more entries via the computer program product comprising: a computer readable medium carrying computer executable instructions for implementing the method, a computer readable medium containing the data stores of one or more entries, and the computer executable instructions, when executed, causing the system to perform a method of providing suggestions within a desired group of foods as selected by the subject based on his unique health profile comprising: obtaining the subject's desired group of food items, querying a database for goodness of all food items that are members of the said group as it relates to the subject's unique health profile, quantifying said goodness as it relates to the subject's unique health profile, sorting the list of said members based on their goodness rating, producing the optimal short list of food suggestions from within the desired group, transmitting said rating to the end user.

It should be understood, however, that the above descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

This invention has many different applications. It can provide nutritional advice to people suffering from one or more conditions. It can also provide nutritional advice to people wishing to follow a particular diet. It can further provide advice on possible activities, alternative remedies and/or life style modifications. The invention is designed to simplify and quantify the overall good or bad attributes of Foods and Nutrients as they relate to various health conditions, health risks, diets and general wellness goals. To establish whether a food item or a nutrient is good for a particular person or not, is a very complicated problem. The invention is designed to address this problem.

Various foods and nutrients found in nature and dishes prepared from them normally contain a variety of vitamins, minerals and other nutrients such as fiber, fat, cholesterol, or carbohydrates. There is always a relationship between these nutrients and various illnesses, health conditions and diets. Sometimes these nutrients are good or serve as a remedy for a condition. Sometimes these nutrients are bad or aggravate a given condition. There have been literally thousands of studies that have taken place to clarify, to prove or to disprove these relationships. For example, Vitamin A has been found to help vision and night blindness, sodium or salt has been found to aggravate high blood pressure, carbohydrates are to be minimized for those following the Atkins diet, and so on.

There is an industry-wide recognition and preference that we should consume these beneficial nutrients as part of our natural diet as opposed to taking them in form of a supplement.

While calories or foods and nutrients rich in calories are to be avoided if one is trying to lose weight, they must be consumed in abundance if one is a cancer patient trying to stop one's weight loss. While the food that is rich in Vitamin A is good for night vision, the same food can be bad for high blood pressure if it contains too much salt. The problem is further complicated by the fact that presence of some substances in one's diet can impact the body's absorption or retention of another nutrient. For example if calcium-rich foods are good for the development or healthy bones and teeth, caffeine-rich and sodium-rich foods can be considered bad for bones and teeth because they increase the body's need for calcium. On the other hand, some nutrients facilitate the absorption or effectiveness of others.

There are virtually infinite permutations of heath conditions, risks and goals that an individual may have. There are also virtually infinite scenarios of nutrients and content level found in natural and prepared foods.

This invention addresses all these complications and infinite possibilities through maintaining information about each nutrient contained within a food item and its level of presence, i.e., foods' richness of the nutrient. The method of the current invention maintains information about how various nutrients in one's diet work with each other or against each other. The invention maintains information about the relationships between various nutrients, food items, life style factors . . . and various health conditions, risks, goals and diets. The invention quantifies these relationships and food content information in a manner that would then enable the user to determine the relative goodness or badness of a given food item for a single health condition as well as for any combination of health conditions, risks, goals, etc. The invention allows the user to address any combination or variation of conditions thereby enabling a total individualized or personalized approach to nutrition. Furthermore, the invention provides such information with unmatched simplicity and brevity that enables its delivery to people's cell phones (and other low bandwidth wireless devices).

Some, but not all, examples of applications or services enabled through the use of this invention include answers to following types of requests. An individual can ask if a given food item is good or bad for his unique health profile. An individual can ask the system to recommend a fish, or a fruit or a vegetable or a dessert that is "best" for his needs based on his unique health profile. An individual can request a list of food items organized by food groups (e.g., seafood, meat, seeds and nuts, dairy products, fruits, vegetables) that are good or bad for him based on his unique health profile. This list can serve as a guide for the user's grocery list. One possible implementation of this invention is based on a relational database composed of the following tables:

1. Item table [such as a list of all nutrients, food items and certain life style considerations such as exercise and smoking];
2. Problem table [such as a list of illnesses, diets, health goals, etc.];
3. Content table [maintains relationship between food items and various nutrients. There is also a numeric factor that represents the food items' level of richness of a particular nutrient. This Factor can have a value of 0 to 5 (or something similar) depending on richness of a particular nutrient in a food item. When possible, the Factor value can be set based on the established RDA for that particular nutrient];
4. Remedy table [maintains information about the relationship between entries in Item (No. 1 above) and Problem table (No. 2 above). There is a Factor that indicates whether an Item is good (a positive value) or bad (a negative value) for a Problem. The value of this factor can be from −10 to +10 or something similar];
5. Anti-Pro table [maintains the relationship between two different entries in the Item table]. A Factor determines the nature of this relationship. If a food item or nutrient works against another, e.g., one nutrient interferes with the other nutrient's absorption, efficacy, body's increased demand for the other, or quicker excretion or metabolism of the other, the factor is negative. If a nutrient or a food item enhances the effects of another, e.g., facilitates absorption, increases efficacy of another, aids in the metabolism of another, then the factor is positive. This Factor can have a value between −5 and +5 or something similar]
6. Group table [maintains information about grouping and hierarchical relationships that exist between entries in Item table, e.g., while both Fish and Tuna may be listed as entries in the Item table, it is important to note that Tuna is a member of Fish group]

The above-mentioned tables are manipulated using four procedures:

"Procedure 1D": Creates new records within the Content table based on existing entries in the Content table for Groups as defined in Group table in No. 6 above. For example if the Beans and Legumes Group item is rich in Fiber (per an entry in Content table) then we create a record for every member of the Beans and Legumes Group (e.g., kidney beans) to reflect its richness in fiber.

"Procedure 2C": Creates new Remedy records based on entries in the Anti-Pro table. If Calcium is good for healthy bones and teeth (the Original Entry), then any food or nutrient that interferes with calcium absorption (as indicated in the Anti-Pro table) is listed as a new entry in the Remedy table with a negative factor value for the health of bones and teeth. The value of the factor can depend on at least one of the values of the factor in the Original Entry and the value of the factor in the Anti-Pro table.

"Procedure 3B": Creates new Remedy records based on the presence of those remedy records that establish a relationship between a Problem and a Group Item. For example if Fish is good for High Cholesterol (the Original Entry), and Tuna is a known member of the Fish Group then the system will automatically create a new Remedy record for Tuna (as member of the Fish group) and High Cholesterol. The factor for this new record can be set based on the factor in the Original Entry.

"Procedure 4A": Creates new records within the Remedy table based on existing entries in the Remedy table and Content table. For example if Vitamin A is necessary for night vision (an existing entry within Remedy table or an Original Entry), then this procedure creates new records (or modifies existing records) that establish a positive (remedy) relationship between night vision (the Problem) and an Item that is rich in Vitamin A per an entry in Content table. The Remedy Factor can be set (for example adjusted upward or downward) based on the factor found in the Original Entry as well as for example the factor found in the corresponding Content table. Upon completion of the execution of this procedure, the remedy factor for each entry in the Remedy table reflects all known relationships between the nutrient content of that Item and the known relationship between those nutrients and the Problem.

"Derived Entries": The Procedures are executed in the order 1D through 4A as shown above. These procedures result in creation of additional entries in the database, which are called Derived Entries. Upon execution of all these procedures a database is provided that can include a complete mapping of all known relationships between various health conditions (i.e., all entries within the Problems table) and various food items (i.e., all entries in the Items table) and a goodness or badness score for each of these pairings (i.e., the Factor value in the Remedy table).

If execution of a procedure can result in modification of an Original Entry, then the modification can be ignored and the original entry can be preserved (i.e., derived entries will never override original entries). For example, if a reliable study suggests that red wine is good for lowering Cholesterol, then the system can ignore any contradiction or modification to that entry which could be suggested, for example, by Procedure 4A due to the red wine's alcohol content or Procedure 2C due to its Anti-Pro properties. Derived entries, however, can revise previously derived entries, and that is how the system is able to take into account all the nutrients contained within a food item and to produce a definitive conclusion or score for a food item's relative goodness or badness for a specific health condition. Upon execution of all the above-mentioned procedures, the system can provide a complete mapping of all known relationships between various health conditions (e.g., all entries within the Problem table) and various food item (e.g., all entries in the Item table) and a goodness or badness score for each of these pairings (e.g., the Factor value in the Remedy table).

Once the system is in place, the system is in a position to handle any inquiry related to the multiple conditions that may uniquely describe an individual's health profile and preferences. For example, if a food item has a negative score for each of the five health conditions that may appear in an individual's health profile, then that food item is less desirable for consumption than the item that has a positive score for each of the five health conditions. As such, the system can establish a composite score for a single food item as it relates to any combination of health conditions. This composite score can serve as the basis for re-ranking when two or more lists come together to make the optimal list. The examples described herein are for illustrative purposes only, and are not intended to limit the scope of the claimed invention.

The invention involves a number of interesting contributions. It can employ, for example, a unique way to organize and represent data, a unique set of procedures to create content for a database, or a unique and simple way to summarize and present that data to the end user.

While the status quo requires that one read pages and pages of literature and web content, memorize an interactable number of nutrient contents, interactions and relationships . . . over a long period of time and after much effort . . . to most likely reach a lesser quality conclusion, this invention can deliver high quality information immediately and in a personalized manner.

The invention claimed is:

1. A method for providing personalized nutritional advice to a subject, the method comprising:
A) obtaining a definition of the subject's medical condition,
B) generating a query for a database for an impact of particular foods and nutrients on the defined medical condition based upon the subject's medical condition wherein the database is stored in a computer system and includes:
   i) a problem table comprising records identifying a plurality of health conditions by which the subject's medical condition is defined wherein the query lists problems unique to the subject,
   ii) an item table comprising an item records for each different food items and nutrients therein,
   iii) a content table that, for each food in said item table, identifies relevant nutrients for the food item and a known nutritional value for that nutrient in the food item, wherein each record in the content table includes a content factor of a value that indicates upon a level of presences of a particular nutrient in the food item,
   iv) an anti-pro table that determines whether one item record in each pair works against or enhances the other item record in each pair of the food item,
   v) a remedy table derived from said problem, content and anti-pro tables and based upon nutritional and medical information, wherein each record in said remedy table identifies one problem from said problem table and for that one problem, information from each relevant content table record from said content table and a factor from said anti-pro table that defines the impact of the food item on the corresponding problem,
   wherein the each remedy table record has a positive or negative value if the item is good or bad, respectively, for the subject's medical condition and have a value that quantifies how good or bad the item will be for the subject's medical condition,
   wherein the factor in each record of the anti-pro table has a positive or negative numerical value depending upon whether one item in the pair enhances or detracts from the efficacy of the other item in the pair, and
C) processing the query in the computer system by:
   i) generating a subject problem list containing those records from the problem table that define the subject's medical condition, and
   ii) generating a subject remedy list of records from the remedy table that corresponds to all the item records that are relevant to the problems in the subject problem list, and
D) generating in the computer system a subject report that lists foods based upon the information in the subject problem list and the subject remedy list that quantifies the impact of different foods and nutrients on the subject's problem list based upon the relationship factors in the remedy list, the subject report defining the impact that the listed foods will have on the problems in the subject problem list.

2. A method as recited in claim 1 wherein the item table further includes records related to illnesses, health conditions, health risks and health goals.

3. A method as recited in claim 1 additionally including a group table in the database that maintains information about relationships that exist between the records in the item table.

4. A method as recited in claim 1 wherein the item table additionally includes item records for life style considerations and each record in the item table is assigned to one of a plurality of categories.

* * * * *